(12) United States Patent
Black

(10) Patent No.: US 9,730,972 B1
(45) Date of Patent: Aug. 15, 2017

(54) SKIN TIGHTENING LOTION

(71) Applicant: Ashley Diana Black International Holdings, LLC, Pearland, TX (US)

(72) Inventor: Ashley D. Black, Pearland, TX (US)

(73) Assignee: Ashley Diana Black International Holdings, LLC, Pearland, TX (US)

( * ) Notice: Subject to any disclaimer, the term of this patent is extended or adjusted under 35 U.S.C. 154(b) by 0 days.

(21) Appl. No.: 15/181,151

(22) Filed: Jun. 13, 2016

(51) Int. Cl.
*A61K 36/00* (2006.01)
*A61K 36/28* (2006.01)
*A61K 8/97* (2017.01)
*A61K 36/886* (2006.01)
*A61K 8/34* (2006.01)
*A61K 8/37* (2006.01)
*A61K 36/899* (2006.01)
*A61K 8/81* (2006.01)
*A61K 8/41* (2006.01)
*A61K 8/36* (2006.01)

(52) U.S. Cl.
CPC ............... *A61K 36/28* (2013.01); *A61K 8/34* (2013.01); *A61K 8/345* (2013.01); *A61K 8/36* (2013.01); *A61K 8/37* (2013.01); *A61K 8/375* (2013.01); *A61K 8/41* (2013.01); *A61K 8/81* (2013.01); *A61K 8/97* (2013.01); *A61K 36/886* (2013.01); *A61K 36/899* (2013.01)

(58) Field of Classification Search
None
See application file for complete search history.

*Primary Examiner* — Qiuwen Mi
(74) *Attorney, Agent, or Firm* — Dentons US LLP

(57) ABSTRACT

Compositions for tightening the skin and reducing muscle pain, bruising, and swelling in skin and methods of forming such compositions.

20 Claims, No Drawings

SKIN TIGHTENING LOTION

FIELD OF THE INVENTION

The principles of the present invention relate generally to compositions and methods of forming such compositions for topical application to the skin, where the compositions include various plant extracts and the use of such compositions provide benefits to the skin, in particular, for application post-treatment of fascia tissue with a fascia tissue treatment device to reduce swelling, bruising, and muscle pain.

BACKGROUND OF THE INVENTION

Fascia is a layer of fibrous connective tissue beneath the skin that attaches, stabilizes, encloses, separates muscles and other internal organs, and performs other functions. The tissue allows for proper functioning of muscles with respect to one another and nerve communications, among other dynamic operations. When fascia tissue becomes damaged by injury, tissue knots, or other medical reasons, it can take time to correct itself. Alternatively, fascia distortions of all types can be repaired by direct manipulation, such as fascial release and/or therapy, to allow for proper functioning of the tissue and allow the underlying muscle as well as other bodily functions to properly operate. In some cases, damaged fascia can be repaired without much difficulty, while in other cases, restoring fascia to its proper form can take considerably more effort. For instance, treatment with a fascia therapy device can cause bruising, swelling, and localized muscle pain. Fascia, when properly treated, can considerably reduce the dimples in skin caused by cellulite, as well as many other cosmetic benefits to the skin and shape of the body.

It is common after fascial release for skin or tissue to bruise or appear to bruise as a result of blood flow. Contusion can be unappealing and long lasting. Pain and swelling may be associated with bruising or the appearance of bruising, and may cause discomfort. In a bruise or appearance of bruising, distress to tissue may cause capillaries to break under the skin, allowing blood to escape and become visible. As time progresses, blood may seep into the surrounding tissues, causing the bruise to darken and spread. Nerve endings within the affected tissue detect the increased pressure which, depending upon the severity and location, may be perceived as pain or pressure.

Means for treating light bruises or their appearance are limited and may include rest, ice, compression, elevation, painkillers and, later in recovery, light stretching exercises. Immediate application of ice while elevating the bruised area may help reduce swelling. Although, the need remains for additional approaches.

Moreover, there is active interest in the cosmetics industry in developing products that may be applied topically to the skin to counteract adverse changes in the skin, such as loosening of skin and bruising. As subcutaneously fat loss occurs, the connective tissue, fibers, and other structures in the dermal and sub-dermal layers can remain, leaving the skin loose. As a result, cosmetic products that reverse or forestall such changes are increasingly in demand as consumers continually seek to improve the appearance of excess skin, muscle pain, bruising, and swelling resulting from treatment with, for example, a fascia tissue device.

BRIEF SUMMARY OF THE INVENTION

The use of a fascia tissue treatment device to treat fascia tissue may lead to swelling and bruising of a user's skin as a result of improving fascia tissue and health. After such a treatment, lotion composition described herein may be used to tighten the skin and reduce muscle pain, bruising, and swelling, and can significantly improve skin aesthetic appearance, such as skin tightening, and would be useful in the formulation of treatments and products for the skin. As described herein, novel and beneficial compositions for the treatment of muscle pain, bruising, skin aesthetic appearance, swelling and the like, are provided along with methods for forming such compositions. The cream may be used anytime regardless of time of application and with or without complimentary other compositions.

One aspect of the present disclosure is the provision of compositions for reducing muscle pain, bruising, swelling, and loose skin following treatment with or without a fascia therapy device. In one embodiment, the composition includes water. In another embodiment, the composition includes *Aloe barbadensis* leaf juice. In yet another embodiment, the composition includes SD Alcohol 40-B. In still another embodiment, the composition includes cetearyl alcohol. In other embodiments, the composition includes glyceryl stearate SE. In yet other embodiments, the composition includes isopropyl myristate. In still other embodiments, the composition includes caprylic/capric triglyceride. In some embodiments, the composition includes propylene glycol. In particular embodiments, the composition includes glycerin. In certain embodiments, the composition includes Ceteareth-20. In one embodiment, the composition includes *Arnica montana* flower extract. In another embodiment, the composition includes oat kernel extract. In one embodiment, the oat kernel extract is from *Avena sativa*. In yet another embodiment, the composition includes tocopheryl acetate. In still another embodiment, the composition includes ammonium acryloyldimethyltaurate/VP copolymer. In other embodiments, the composition includes disodium EDTA. In yet other embodiments, the composition includes phenoxyethanol. In still other embodiments, the composition includes caprylyl glycol. In some embodiments, the composition includes ethylexylglycerin. In particular embodiments, the composition includes hexylene glycol. In certain embodiments, the composition includes fragrance. In one embodiment, the composition includes citric acid.

In some embodiments, the water is from about 55%, about 56%, about 57%, about 58%, about 59%, about 60%, about 61%, about 62%, about 63%, about 64%, about 65%, about 66%, about 67%, about 68%, about 69%, about 70%, about 71%, about 72%, about 73%, about 74%, about 75%, about 76%, about 77%, about 78%, about 79%, about 80%, about 81%, about 82%, about 83%, about 84%, or about 85% of the total weight by volume of the composition. In another embodiment, the *Aloe barbadensis* leaf juice is from about 5.0%, about 5.5%, about 6.0%, about 6.5%, about 7.0%, about 7.5%, about 8.0%, about 8.5%, about 9.0%, about 9.5%, or about 10.0% of the total weight by volume of the composition. In yet another embodiment, the SD Alcohol 40-B is from about 1.0%, about 1.5%, about 2.0%, about 2.5%, about 3.0%, about 3.5%, or about 4.0% of the total weight by volume of the composition. In still another embodiment, the cetearyl alcohol is from about 1.0%, about 1.5%, about 2.0%, about 2.5%, about 3.0%, about 3.5%, or about 4.0% of the total weight by volume of the composition. In other embodiments, the glyceryl stearate SE is from about 1.0%, about 1.5%, about 2.0%, about 2.5%, about 3.0%, about 3.5%, or about 4.0% of the total weight by volume of the composition. In yet other embodiments, the isopropyl myristate is from about 1.0%, about 1.5%, about 2.0%, about 2.5%, about 3.0%, about 3.5%, or about 4.0% of the total weight by volume of the composition. In still other embodiments, the caprylic/capric triglyceride is from about 1.0%, about 1.5%, about 2.0%, about 2.5%, about 3.0%, about 3.5%, or about 4.0% of the total weight by volume of the composition. In some embodiments, the propylene glycol is from about 1.0%, about 1.5%, about 2.0%, about 2.5%, about 3.0%, about 3.5%, or about 4.0% of the total weight by volume of the composition. In particular embodiments, the glycerin is from about 1.0%, about 1.5%, about 2.0%, about 2.5%, about 3.0%, about 3.5%, or about 4.0% of the total weight by volume of the composition. In certain embodiments, the Ceteareth-20 is from about 1.0%, about 1.5%, about 2.0%, about 2.5%, about 3.0%, about 3.5%, or about 4.0% of the total weight by volume of the composition. In one embodiment, the *Arnica montana* flower extract is from about 0.1%, about 0.2%, about 0.3%, about 0.4%, about 0.5%, about 0.6%, about 0.7%, about 0.8%, or about 0.9% of the total weight by volume of the composition. In another embodiment, the oat kernel extract is from about 0.1%, about 0.2%, about 0.3%, about 0.4%, about 0.5%, about 0.6%, about 0.7%, about 0.8%, or about 0.9% of the total weight by volume of the composition. In yet another embodiment, the tocopheryl acetate is from about 0.1%, about 0.2%, about 0.3%, about 0.4%, about 0.5%, about 0.6%, about 0.7%, about 0.8%, or about 0.9% of the total weight by volume of the composition. In still another embodiment, the ammonium acryloyldimethyltaurate/VP copolymer is from about 0.1%, about 0.2%, about 0.3%, about 0.4%, about 0.5%, about 0.6%, about 0.7%, about 0.8%, or about 0.9% of the total weight by volume of the composition. In other embodiments, the disodium EDTA is from about 0.01%, about 0.02%, about 0.03%, about 0.04%, about 0.05%, about 0.06%, about 0.07%, about 0.08%, or about 0.09% of the total weight by volume of the composition. In yet other embodiments, the phenoxyethanol is from about 0.1%, about 0.2%, about 0.3%, about 0.4%, about 0.5%, about 0.6%, about 0.7%, about 0.8%, or about 0.9% of the total weight or volume of the composition. In still other embodiments, the caprylyl glycol is from about 0.1%, about 0.2%, about 0.3%, about 0.4%, about 0.5%, about 0.6%, about 0.7%, about 0.8%, or about 0.9% of the total weight by volume of the composition. In some embodiments, the ethylexylglycerin is from about 0.01%, about 0.02%, about 0.03%, about 0.04%, about 0.05%, about 0.06%, about 0.07%, about 0.08%, or about 0.09% of the total weight by volume of the composition. In particular embodiments, the hexylene glycol is from about 0.01%, about 0.02%, about 0.03%, about 0.04%, about 0.05%, about 0.06%, about 0.07%, about 0.08%, or about 0.09% of the total weight by volume of the composition. In certain embodiments, the fragrance is from about 0.01%, about 0.02%, about 0.03%, about 0.04%, about 0.05%, about 0.06%, about 0.07%, about 0.08%, or about 0.09% of the total weight by volume of the composition. In one embodiment, the citric acid is from about 0.01%, about 0.02%, about 0.03%, about 0.04%, about 0.05%, about 0.06%, about 0.07%, about 0.08%, or about 0.09% of the total weight by volume of the composition.

In some embodiments, the composition can be stored in a dispenser. In one embodiment, the dispenser can be integrated into or onto the fascia therapy device. In an alternative embodiment, the dispenser can include a member that functions to dispense the composition in a roll-on, sponge applicator, or other dispensing technique. A cartridge that includes the composition can be used and positioned within a dispensing mechanism of the fascia therapy device. In particular embodiments, the composition can be applied from a dispenser. The cream can be dispersed in unlimited ways.

Another aspect of the present disclosure is the provision of a method of forming a composition for tightening the skin and reducing muscle pain, bruising, swelling to significantly improve skin aesthetic appearance while lubricating skin after treatment with a fascia therapy device or any other time, whether or not a fascia treatment is performed. In one embodiment, the method comprises mixing water, *Aloe barbadensis* leaf juice, SD Alcohol 40-B, cetearyl alcohol, glyceryl stearate SE, isopropyl myristate, caprylic/capric triglyceride, propylene glycol, glycerin, Ceteareth-20, *Arnica montana* flower extract, oat kernel extract, tocopheryl acetate, ammonium acryloyldimethyltaurate/VP copolymer, disodium EDTA, phenoxyethanol, caprylyl glycol, ethylexylglycerin, hexylene glycol, fragrance, citric acid, or any combination thereof.

DETAILED DESCRIPTION OF THE INVENTION

A combination of ingredients, with a surprisingly pleasant aroma, have been found to synergistically reduce loose skin, muscle pain, bruising, and swelling over a period of time, following treatment with a fascia therapy device or any other time. Treatment with a fascia therapy device can produce better results of certain conditions, such as reducing subcutaneous fat, improving blood flow, and many other conditions. A fascia tissue treatment device, as described in U.S. Patent Application No. 2014/0243718, can include a bar and a plurality of flower-like or claw-shaped element(s) connected to the bar along a plane. The flower-like elements can each include multiple fingers that are stiff and extend outward from the bar. Without being bound by theory, it is believed that at least one of the ingredients in the oil or lotion described herein work to suppress inflammatory processes in the body for muscle pain, bruising, and swelling reducing effects following application and use of the fascia tissue treatment device. The oil or lotion described herein may also be used as a standalone solution to suppress inflammatory processes and so forth. In particular, the oil or lotion composition may mitigate subcutaneous inflammatory processes, thereby reducing muscle pain, bruising, and swelling while suppressing the uniquely unpleasant odor typical of *arnica* flower extract. A dermatologically acceptable vehicle was discovered that provides a stable environment for the active ingredients, and a pleasant scent and tactile property may be provided when applied to skin. Because the cream provides for the pleasant scent, a common resistance of users of certain ingredients may be reduced or eliminated.

The principles described herein relate to compositions for reducing muscle pain, bruising, swelling, and loose skin having a pleasant odor, for application to skin post-treatment of a fascia tissue treatment device or any other time. In one embodiment, the composition includes the active ingredients *Arnica montana* flower extract, caprylic/capric triglyceride, and tocopherol. In particular embodiments, to provide a satisfying and pleasant aroma in addition to adequate soothing relief post-treatment with a fascia tissue treatment device, the composition includes additional compounds in conjunction with active ingredients. In some embodiments, the composition includes water, *Aloe barbadensis* leaf juice, SD Alcohol 40-B, cetearyl alcohol, glyceryl stearate SE, isopropyl myristate, caprylic/capric triglyceride, propylene glycol, glycerin, Ceteareth-20, *Arnica montana* flower extract, oat kernel extract, tocopheryl acetate, ammonium acryloyldimethyltaurate/VP copolymer, disodium EDTA, phenoxyethanol, caprylyl glycol, ethylexylglycerin, hexylene glycol, fragrance, citric acid, or any combination thereof. The compositions can include any number of combinations of additional ingredients described throughout this specification. The concentrations of the any ingredient within the compositions can vary. In non-limiting embodiments, for example, the compositions can comprise, consisting essentially of, or consist of, in their final form, for example, about 0.01% to about 85.00% or any range derivable therein, of at least one of the ingredients that are described throughout the specification and claims. The percentage can be calculated by weight of the total composition. Comparable percentages may be provided for by volume of the total composition. A person of ordinary skill in the art would understand that the concentrations can vary depending on the addition, substitution, and/or subtraction of ingredients in a given composition.

The disclosed compositions can also include various antioxidants to retard oxidation of one or more components. Additionally, the prevention of the action of microorganisms can be brought about by preservatives, such as various antibacterial and antifungal agents. Further, the disclosed compositions can also include cosmetic ingredients, UV absorption agents, moisturizing agents, structuring agents, emulsifiers, thickening agents, and pharmaceutical ingredients.

The disclosed compositions can be incorporated into all types of formulations. Non-limiting examples of suitable formulations include emulsions (e.g., water-in-oil, water-in-oil-in-water, oil-in-water, silicone-in-water, water-in-silicone, oil-in-water-in-oil, oil-in-water-in-silicone emulsions), creams, lotions, solutions (both aqueous and hydroalcoholic), anhydrous bases (such as lipsticks and powders), gels, and ointments or by other method or any combination of the forgoing as would be known to one of ordinary skill in the art. Variations and other appropriate formulations will be apparent to the skilled artisan and are appropriate for use in the present invention. In certain embodiments, the concentrations and combinations of the compounds, ingredients, and agents may be selected in such a way that the combinations are chemically compatible and do not form complexes that precipitate from the finished product.

It is also contemplated that ingredients identified throughout this specification, including but not limited to *Arnica montana* flower extract, caprylic/capric triglyceride, and tocopherol, or any combinations thereof, can be individually or combinatorially encapsulated for delivery to a target area, such as skin. Non-limiting examples of encapsulation techniques include the use of liposomes, vesicles, and/or nanoparticles (e.g., biodegradable and non-biodegradable colloidal particles comprising polymeric materials in which the ingredient is trapped, encapsulated, and/or absorbed) that can be used as delivery vehicles to deliver the ingredient to skin. See, e.g., U.S. Pat. Nos. 6,387,398; 6,203,802; and 5,411,744.

The principles described herein also relate to a process of forming a composition to reduce muscle pain, bruising, swelling, and loose skin while both lubricating the skin for application of a fascia therapy device and having a pleasant odor and mitigating the unpleasant odor of the active ingredients. In certain embodiments, the process includes mixing water, *Aloe barbadensis* leaf juice, SD Alcohol 40-B, cetearyl alcohol, glyceryl stearate SE, isopropyl myristate, caprylic/capric triglyceride, propylene glycol, glycerin, Ceteareth-20, *Arnica montana* flower extract, oat kernel extract, tocopheryl acetate, ammonium acryloyldimethyltaurate/VP copolymer, disodium EDTA, phenoxyethanol, caprylyl glycol, ethylexylglycerin, hexylene glycol, fragrance, citric acid, or any combination thereof.

Definitions and methods described herein are provided to better define the present disclosure and to guide those of ordinary skill in the art in the practice of the present disclosure. Unless otherwise noted, terms are to be understood according to conventional usage by those of ordinary skill in the relevant art.

In some embodiments, numbers expressing quantities of ingredients, properties such as molecular weight, reaction conditions, and so forth, used to describe and claim certain embodiments of the present disclosure are to be understood as being modified in some instances by the term "about." In some embodiments, the term "about" is used to indicate that a value includes the standard deviation of the mean for the device or method being employed to determine the value. In some embodiments, the numerical parameters set forth in the written description and attached claims are approximations that can vary depending upon the desired properties sought to be obtained by a particular embodiment. In some embodiments, the numerical parameters should be construed in light of the number of reported significant digits and by applying ordinary rounding techniques. Notwithstanding that the numerical ranges and parameters setting forth the broad scope of some embodiments of the present disclosure are approximations, the numerical values set forth in the specific examples are reported as precisely as practicable. The numerical values presented in some embodiments of the present disclosure may contain certain errors necessarily resulting from the standard deviation found in their respective testing measurements. The recitation of ranges of values herein is merely intended to serve as a shorthand method of referring individually to each separate value falling within the range. Unless otherwise indicated herein, each individual value is incorporated into the specification as if it were individually recited herein.

In some embodiments, the terms "a" and "an" and "the" and similar references used in the context of describing a particular embodiment (especially in the context of certain of the following claims) can be construed to cover both the singular and the plural, unless specifically noted otherwise. In some embodiments, the term "or" as used herein, including the claims, is used to mean "and/or" unless explicitly indicated to refer to alternatives only or the alternatives are mutually exclusive.

The terms "comprise," "have" and "include" are open-ended linking verbs. Any forms or tenses of one or more of these verbs, such as "comprises," "comprising," "has," "having," "includes" and "including," are also open-ended. For example, any method that "comprises," "has" or "includes" one or more steps is not limited to possessing only those one or more steps and can also cover other unlisted steps. Similarly, any composition or device that "comprises," "has" or "includes" one or more features is not limited to possessing only those one or more features and can cover other unlisted features.

All methods described herein can be performed in any suitable order unless otherwise indicated herein or otherwise clearly contradicted by context. The use of any and all examples, or exemplary language (e.g., "such as") provided with respect to certain embodiments herein is intended merely to better illuminate the present disclosure and does not pose a limitation on the scope of the present disclosure otherwise claimed. No language in the specification should be construed as indicating any non-claimed element essential to the practice of the present disclosure.

Groupings of alternative elements or embodiments of the present disclosure disclosed herein are not to be construed as limitations. Each group member can be referred to and claimed individually or in any combination with other members of the group or other elements found herein. One or more members of a group can be included in, or deleted from, a group for reasons of convenience or patentability. When any such inclusion or deletion occurs, the specification is herein deemed to contain the group as modified thus fulfilling the written description of all Markush groups used in the appended claims.

All publications, patents, patent applications, and other references cited in this application are incorporated herein by reference in their entirety for all purposes to the same extent as if each individual publication, patent, patent application or other reference was specifically and individually indicated to be incorporated by reference in its entirety for all purposes. Citation of a reference herein shall not be construed as an admission that such is prior art to the present disclosure.

Having described the present disclosure in detail, it will be apparent that modifications, variations, and equivalent embodiments are possible without departing the scope of the present disclosure defined in the appended claims. Furthermore, it should be appreciated that all examples in the present disclosure are provided as non-limiting examples.

EXAMPLES

The following non-limiting examples are provided to further illustrate the present disclosure. It should be appreciated by those of skill in the art that the techniques disclosed in the examples that follow represent approaches that have been found to function well in the practice of the present disclosure, and thus can be considered to constitute examples of modes for its practice. However, those of skill in the art should, in light of the present disclosure, appreciate that many changes can be made in the specific embodiments that are disclosed and still obtain a like or similar result without departing from the spirit and scope of the present disclosure.

Example 1: Compounds

Loose skin, muscle pain, bruising, and swelling can be reduced using the active ingredient Arnica Montana flower extract optionally post-treatment of a user with fascia tissue treatment device. A composition comprising water, *Aloe barbadensis* leaf juice, SD Alcohol 40-B, cetearyl alcohol, glyceryl stearate SE, isopropyl myristate, caprylic/capric triglyceride, propylene glycol, glycerin, Ceteareth-20, Arnica Montana flower extract, oat kernel extract, tocopheryl acetate, ammonium acryloyldimethyltaurate/VP copolymer, disodium EDTA, phenoxyethanol, caprylyl glycol, ethylexylglycerin, hexylene glycol, fragrance, and citric acid can visibly reduce the unsightly effects of loose skin, muscle pain, bruising, and swelling following repeated topical applications during and/or after use of a fascia therapy device.

The composition can include:

| INCI Name | Percent (wt/vol %) |
| --- | --- |
| water (Aqua) | 55.0-85.0 |
| *Aloe barbadensis* leaf juice | 5.0-10.0 |
| SD Alcohol 40-B | 1.0-4.0 |

-continued

| INCI Name | Percent (wt/vol %) |
| --- | --- |
| cetearyl alcohol | 1.0-4.0 |
| glyceryl stearate SE | 1.0-4.0 |
| isopropyl myristate | 1.0-4.0 |
| caprylic/capric triglyceride | 1.0-4.0 |
| propylene glycol | 1.0-4.0 |
| glycerin | 1.0-4.0 |
| Ceteareth-20 | 1.0-4.0 |
| *Arnica montana* flower extract | 0.1-0.9 |
| *Avena sativa* kernel extract | 0.1-0.9 |
| tocopheryl acetate | 0.1-0.9 |
| ammonium acryloyldimethyltaurate/VP copolymer | 0.1-0.9 |
| disodium EDTA | 0.01-0.09 |
| phenoxyethanol | 0.1-0.9 |
| caprylyl glycol | 0.1-0.9 |
| ethylexylglycerin | 0.01-0.09 |
| hexylene glycol | 0.01-0.09 |
| fragrance | 0.01-0.09 |
| citric acid | 0.01-0.09 |
| Total | 100.00 |

Example 2: Compound Preparation

To prepare a dermatologically acceptable vehicle that provides a chemically stable and cosmetically acceptable environment for the ingredients capable of reducing loose skin, muscle pain, bruising, swelling and lubricating the skin during an optional usage or application of a fascia therapy device, Arnica Montana flower extract can be mixed with water, *Aloe barbadensis* leaf juice, SD Alcohol 40-B, cetearyl alcohol, glyceryl stearate SE, isopropyl myristate, caprylic/capric triglyceride, propylene glycol, glycerin, Ceteareth-20, oat kernel extract, tocopheryl acetate, ammonium acryloyldimethyltaurate/VP copolymer, disodium EDTA, phenoxyethanol, caprylyl glycol, ethylexylglycerin, hexylene glycol, fragrance, and citric acid.

The amount of each ingredient can vary. For example, the composition can include water from about 55.0% to about 85.0%; *Aloe barbadensis* leaf juice from about 5.0% to about 10.0%; SD Alcohol 40-B from about 1.0% to about 4.0%; cetearyl alcohol from about 1.0% to about 4.0%; glyceryl stearate SE from about 1.0% to about 4.0%; isopropyl myristate from about 1.0% to about 4.0%; caprylic/capric triglyceride from about 1.0% to about 4.0%; propylene glycol from about 1.0% to about 4.0%; glycerin from about 1.0% to about 4.0%; Ceteareth-20 from about 1.0% to about 4.0%; Arnica Montana flower extract from about 0.1% to about 0.9%; oat kernel extract from about 0.1% to about 0.9%; tocopheryl acetate from about 0.1% to about 0.9%; ammonium acryloyldimethyltaurate/VP copolymer from about 0.1% to about 0.9%; disodium EDTA from about 0.01% to about 0.09%; phenoxyethanol from about 0.1% to about 0.9%; caprylyl glycol from about 0.1% to about 0.9%; ethylexylglycerin from about 0.01% to about 0.09%; hexylene glycol from about 0.01% to about 0.09%; fragrance from about 0.01% to about 0.09%; and citric acid from about 0.01% to about 0.09% of the total weight by volume of the entire composition.

As various modifications could be made in the compositions and methods herein described without departing from the scope of the invention, it is intended that all matter contained in the foregoing description shall be interpreted as illustrative rather than limiting. The breadth and scope of the present invention should not be limited by any of the above-described exemplary embodiments, but should be defined only in accordance with the following claims appended hereto and their equivalents. All patent and non-patent documents cited in this specification are incorporated herein by reference in their entireties.

What is claimed:

1. A composition comprising water, *Aloe barbadensis* leaf juice, SD Alcohol 40-B, cetearyl alcohol, glyceryl stearate SE, isopropyl myristate, caprylic/capric triglyceride, propylene glycol, glycerin, Ceteareth-20, *Arnica montana* flower extract, oat kernel extract, tocopheryl acetate, ammonium acryloyldimethyltaurate/VP copolymer, disodium EDTA, phenoxyethanol, caprylyl glycol, ethylhexylglycerin, hexylene glycol, fragrance, and citric acid, wherein the water is from about 55.0% to about 85.0%, the *Aloe barbadensis* leaf juice is from about 5.0% to about 10.0%, the SD Alcohol 40-B is from about 1.0% to about 4.0%, the cetearyl alcohol is from about 1.0% to about 4.0%, the glyceryl stearate SE is from about 1.0% to about 4.0%, the isopropyl myristate is from about 1.0% to about 4.0%, the caprylic/capric triglyceride is from about 1.0% to about 4.0%, the propylene glycol is from about 1.0% to about 4.0%, the glycerin is from about 1.0% to about 4.0%, the Ceteareth-20 is from about 1.0% to about 4.0%, the *Arnica montana* flower extract is from about 0.1% to about 0.9%, the oat kernel extract is from about 0.1% to about 0.9%, the tocopheryl acetate is from about 0.1% to about 0.9%, the ammonium acryloyldimethyltaurate/VP copolymer is from about 0.1% to about 0.9%, the disodium EDTA is from about 0.01% to about 0.09%, the phenoxyethanol is from about 0.1% to about 0.9%, the caprylyl glycol is from about 0.1% to about 0.9%, the ethylhexylglycerin is from about 0.01% to about 0.09%, the hexylene glycol is from about 0.01% to about 0.09%, the fragrance is from about 0.01% to about 0.09%, and the citric acid is from about 0.01% to about 0.09% of the total weight by volume of the composition.

2. The composition according to claim 1, wherein the oat kernel extract is from *Avena sativa*.

3. The composition of claim 1, further comprising an antioxidant.

4. The composition of claim 1, further comprising a UV adsorption agent.

5. The composition of claim 1, further comprising an antibacterial agent.

6. The composition of claim 1, further comprising an antifungal agent.

7. The composition of claim 1, further comprising a moisturizing agent.

8. The composition of claim 1, further comprising an emulsifier.

9. The composition of claim 1, further comprising a thickening agent.

10. The composition of claim 1, further comprising a structuring agent.

11. The composition of claim 1, further comprising a pharmaceutical ingredient.

12. The composition of claim 1, wherein the composition is in the form of a cream.

13. The composition of claim 1, wherein the composition is in the form of a gel.

14. The composition of claim 1, wherein the composition is in the form of an anhydrous base.

15. A composition comprising water, *Aloe barbadensis* leaf juice, SD Alcohol 40-B, cetearyl alcohol, glyceryl stearate SE, isopropyl myristate, caprylic/capric triglyceride, propylene glycol, glycerin, Ceteareth-20, *Arnica montana* flower extract, oat kernel extract, tocopheryl acetate, ammonium acryloyldimethyltaurate/VP copolymer, disodium EDTA, phenoxyethanol, caprylyl glycol, ethylhexylglycerin, hexylene glycol, fragrance, and citric acid, wherein the composition is in the form of an emulsion.

16. The composition of claim 15, further comprising an antioxidant.

17. The composition of claim 15, further comprising a pharmaceutical ingredient.

18. A composition comprising water, *Aloe barbadensis* leaf juice, SD Alcohol 40-B, cetearyl alcohol, glyceryl stearate SE, isopropyl myristate, caprylic/capric triglyceride, propylene glycol, glycerin, Ceteareth-20, *Arnica montana* flower extract, oat kernel extract, tocopheryl acetate, ammonium acryloyldimethyltaurate/VP copolymer, disodium EDTA, phenoxyethanol, caprylyl glycol, ethylhexylglycerin, hexylene glycol, fragrance, and citric acid, wherein the composition is in the form of a lotion.

19. The composition of claim 18, further comprising an antioxidant.

20. The composition of claim 18, further comprising a pharmaceutical ingredient.

* * * * *